United States Patent
Khalaj

(10) Patent No.: US 9,517,327 B2
(45) Date of Patent: Dec. 13, 2016

(54) CATHETER-POSITIONING SLIDE COVER CLAMP ASSEMBLY

(71) Applicant: AVENT, INC., Alpharetta, GA (US)

(72) Inventor: Steve S. Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 350 days.

(21) Appl. No.: 14/037,711

(22) Filed: Sep. 26, 2013

(65) Prior Publication Data

US 2015/0088075 A1 Mar. 26, 2015

(51) Int. Cl.
*A61M 25/02* (2006.01)

(52) U.S. Cl.
CPC ........ *A61M 25/02* (2013.01); *A61M 2025/024* (2013.01); *A61M 2025/028* (2013.01); *A61M 2025/0246* (2013.01)

(58) Field of Classification Search
CPC ............ A61M 25/02; A61M 2025/024; A61M 2025/0246; A61M 2025/028
See application file for complete search history.

(56) References Cited

U.S. PATENT DOCUMENTS

| 5,690,616 A | 11/1997 | Mogg | |
|---|---|---|---|
| 7,749,199 B2 | 7/2010 | Mogg | |
| 2013/0018319 A1* | 1/2013 | Abe | A61M 25/02 604/174 |
| 2013/0131600 A1* | 5/2013 | Mogg | A61M 25/02 604/174 |

FOREIGN PATENT DOCUMENTS

| GB | 2 288 542 A | 10/1995 |
|---|---|---|
| WO | WO 03/068304 A1 | 8/2003 |
| WO | WO 2005/079903 A2 | 9/2005 |
| WO | WO 2008/119041 A1 | 10/2008 |
| WO | WO 2012/020246 A1 | 2/2012 |

OTHER PUBLICATIONS

PCT Search Report and Written Opinion, Nov. 18, 2014.

\* cited by examiner

*Primary Examiner* — Nathan R Price
*Assistant Examiner* — Anh Bui
(74) *Attorney, Agent, or Firm* — Dority & Manning, P.A.

(57) ABSTRACT

The present invention provides a catheter clamp assembly having a base and a slide cover. The base has a top, bottom and a body including a slide cover track. The body has internal walls defining a catheter opening extending from the bottom to the top. A catheter channel extends from the catheter opening to a sidewall opening. The slide cover includes a lower surface incorporating a prong to engage a wall defining the catheter opening and to secure a catheter in the catheter channel. The slide cover has a first location providing access to the catheter opening and a second location that clamps a catheter in the catheter channel. Moving the slide cover from its first location contacts a length of catheter extending through the catheter opening to position it in the catheter channel for securement when the slide cover reaches its second location.

20 Claims, 11 Drawing Sheets

CATHETER-POSITIONING SLIDE COVER CLAMP ASSEMBLY

FIELD OF THE INVENTION

The present invention relates generally to a catheter clamps for attaching catheters to patients' skin at an insertion site.

BACKGROUND OF THE INVENTION

Infusion catheters for delivery of fluid medication into anatomical systems, such as the human body, are known in the art. Such catheters generally include a flexible hollow tube inserted into some region of the anatomy. The tube typically contains one or more axial lumens within which the fluid may flow. The proximal end of the catheter tube is connected to a fluid source from which fluid is introduced into the catheter tube. The fluid flows within one of the lumens under pressure supplied at the proximal end of the tube. For each lumen, there are commonly provided one or more exit holes along an infusion section near the distal end of the tube, for fluid to exit the tube.

Such infusion catheters are typically inserted into a tunnel or opening into the skin. The catheter extends into the anatomy to a site where it is desirable to deliver fluid medication. After a catheter is inserted, it is important to maintain the catheter in position to properly deliver the fluid medication. Infusion catheters are typically small-diameter flexible tubes that can be easily pulled out or disturbed if they are not well secured. In the past, catheters have been sutured to the skin or secured in place by various techniques utilizing adhesive tape. These techniques provide inconsistent results and can result in movement of the catheter, leakage of fluid medication at the point of insertion, kinking of the catheter that may reduce or obstruct fluid flow.

Various catheter clamps have been proposed to address the shortcomings of traditional catheter securing techniques. For example, U.K. Patent Application GB 2,288,542 for a "Catheter Clamp" published Oct. 25, 1995 describes a catheter clamp having an base with an opening or hole for threading the catheter through and a curved catheter support that engages with a pivotable arm that grips the catheter between a vertical wall and a portion of the arm when the arm is rotated. In an embodiment of the clamp, a slider that locks in position is used to hold the catheter securely against a vertical wall. In both embodiments, the catheter must be manually aligned in the correct position to avoid kinks or damage when the clamp is engaged. For example, an improperly aligned catheter can be crimped, pinched or even severed by the pivoting arm of the clamp. As another example, the slider embodiment of the clamp requires a user to manually align the lock in a channel through a pair of retention pins prior to engaging the slider against a vertical wall of body block to hold the catheter. Failure to properly align the catheter in the channel could cause the catheter to be pinched or kinked while moving the slider and may also prevent the laterally projecting elements of the locking pins from properly seating to engage the slider in its clamping position.

Another catheter clamp is described in U.S. Pat. No. 7,749,199 issued Jul. 6, 2010, for a "Catheter Clamp" describes a low-profile catheter clamp having an base with an opening or hole for threading the catheter through, a portion for bending a catheter through an arc, a ribbed channel in the base, and a pivotable cap that acts upon the catheter to clamp the catheter against the base. In order to use the clamp, a catheter is threaded through the hold and must be manually aligned in the channel prior to closing the cap to clamp the catheter against the base. If the catheter is not properly aligned or positioned in the channel, the catheter may be pinched or kinked when the cap is closed.

Accordingly, there is a need for a practical and cost-effective catheter clamp that is easy to use and that avoids pinking or kinking a catheter when the clamp is engaged. There is also a need for a practical and cost-effective catheter clamp that does not require a separate step of manual alignment or positioning of the catheter in the clamp prior to engaging the clamp to secure the catheter. Meeting these needs is important because catheters are many times more expensive than the catheter clamp. Moreover, the catheter is engaged in the clamp after it is positioned in a patient. Crimping or kinking a catheter may require a physical to remove and replace the damaged catheter incurring additional expense of time and medical supplies and exposing a patient to increased risk of infection or trauma.

SUMMARY OF THE INVENTION

Generally stated, the present invention provides a catheter clamp assembly that includes a base and a slide cover. The slide cover has a first location to provide access to thread a catheter through the clamp assembly and a second location that clamps a catheter in a catheter channel. Moving the slide cover from its first location contacts a length of catheter extending through a catheter opening and positions it in the catheter channel for securement when the slide cover reaches its second location while avoiding any kinking or pinching of the catheter.

The clamp assembly has base that includes a bottom, a top, and a body having a slide cover track. The body has internal walls defining a catheter opening extending from the bottom to the top. The body further defines a catheter channel extending from the catheter opening to a sidewall exit. In an aspect of the invention, the internal walls defining the catheter opening may further define a generally curved transition between the catheter opening and the catheter channel.

The clamp assembly has a slide cover that is engaged with the slide cover track of the base. The slide cover includes a prong extending from a lower surface of the slide cover to engage with a wall defining the catheter opening and for clamping a catheter in the catheter channel. The slide cover has a first location for providing access to thread a catheter through the catheter opening and a second location that securely clamps a catheter in the catheter channel, such that sliding the slide cover from its first location to its second location contacts a length of a catheter extending through the catheter opening and positioned it in the catheter channel for securement when the slide cover reaches its second position.

According to an aspect of the invention, the slide cover track may be a pair of opposed sides of the body of the base, the opposed sides having recesses defined therein. The recesses defined in the opposed sides of the body of the base may further include stops to limit movement of the slide cover to the location of the stops. The slide cover may further include an upper surface, a first edge and an opposed second edge. The slide cover may incorporate catches on the first and second edges for slidably engaging the slide cover with the recesses defined in the body of the base. In another aspect of the invention, the slide cover may include an edge having curved or chamfered portion for contacting a catheter. For example, the slide cover may include a third edge that is generally perpendicular to the first edge and the second edge and this third edge may have a curved or chamfered portion for contacting a catheter. The slide cover may include a lip or projection for better engaging the finger of a user when applying for to slide the slide cover. This lip or projection may extend from an upper surface of the slide cover.

In another aspect of the invention, the top surface of the base may further include a notch, channel or recess for receiving the prong extending from the lower surface of the cover. Desirably, the recess is located on the top surface of the base to releasably hold the slide cover in its first location. The prong extending from the lower surface of the slide cover may have a portion including an incline, curve or similar shape. The shaped portion of the prong may be desirable for securely engaging a catheter against the catheter channel. Desirably, the prong will engage a catheter against a generally curved transition between the catheter opening and the catheter channel.

The present invention also encompasses a catheter system composed of a flexible catheter such as, for example, an infusion catheter, and a catheter clamp assembly as described above.

A better understanding of the above and many other features and advantages of the new inflatable retention system for an enteral feeding tube and for the new enteral feeding tube assembly incorporating such an inflatable retention system may be obtained from a consideration of the detailed description of the invention below, particularly if such consideration is made in conjunction with the appended drawings.

DEFINITIONS

Figure 1:
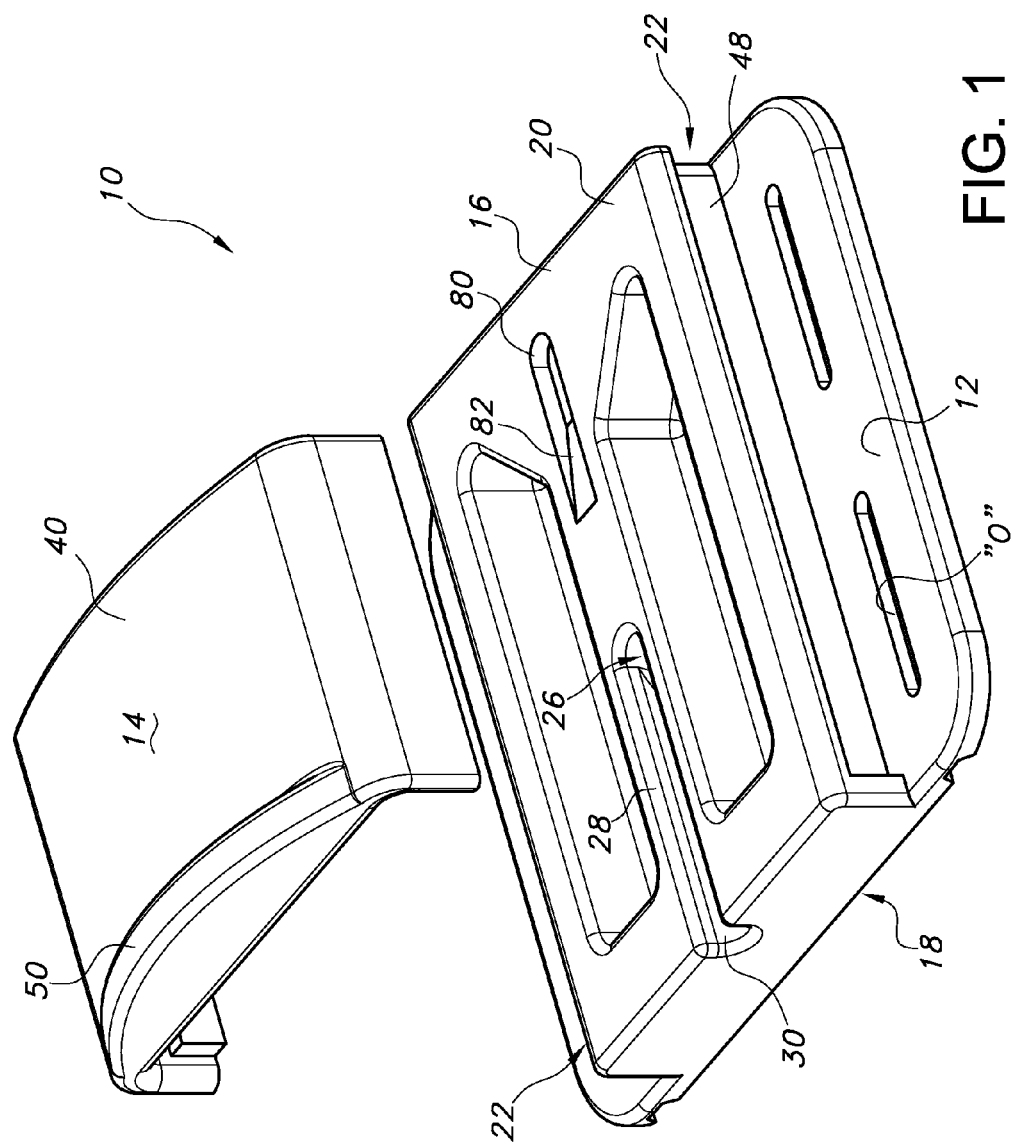
FIG. 1 shows an exploded perspective view of an exemplary catheter-positioning slide cover clamp assembly.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the terms "position," and/or "positioned," refers to the spatial property possessed by an arrangement or location of things in a particular relationship, alignment, formation or conformation.

As used herein, the terms "orientation" or "position" used interchangeably herein refer to the spatial property of a place where something is situated or a way in which something is situated; for example, "the position of the hands on the clock."

As used herein, the term "about" adjacent to a stated number refers to an amount that is plus or minus ten (10) percent of the stated number.

DETAILED DESCRIPTION OF THE INVENTION

The invention(s) disclosed herein relate generally to a catheter clamp system. More particularly, the invention(s) disclosed herein relate to a catheter clamp system that includes a base and a slide cover. The slide cover has a first location on the base to provide access to thread a catheter through the clamp assembly and a second location on the base that clamps a catheter in a catheter channel. Moving the slide cover from its first location contacts a length of catheter extending through a catheter opening and positions it in the catheter channel for securement when the slide cover reaches its second location while avoiding any kinking or pinching of the catheter.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Figure 2:
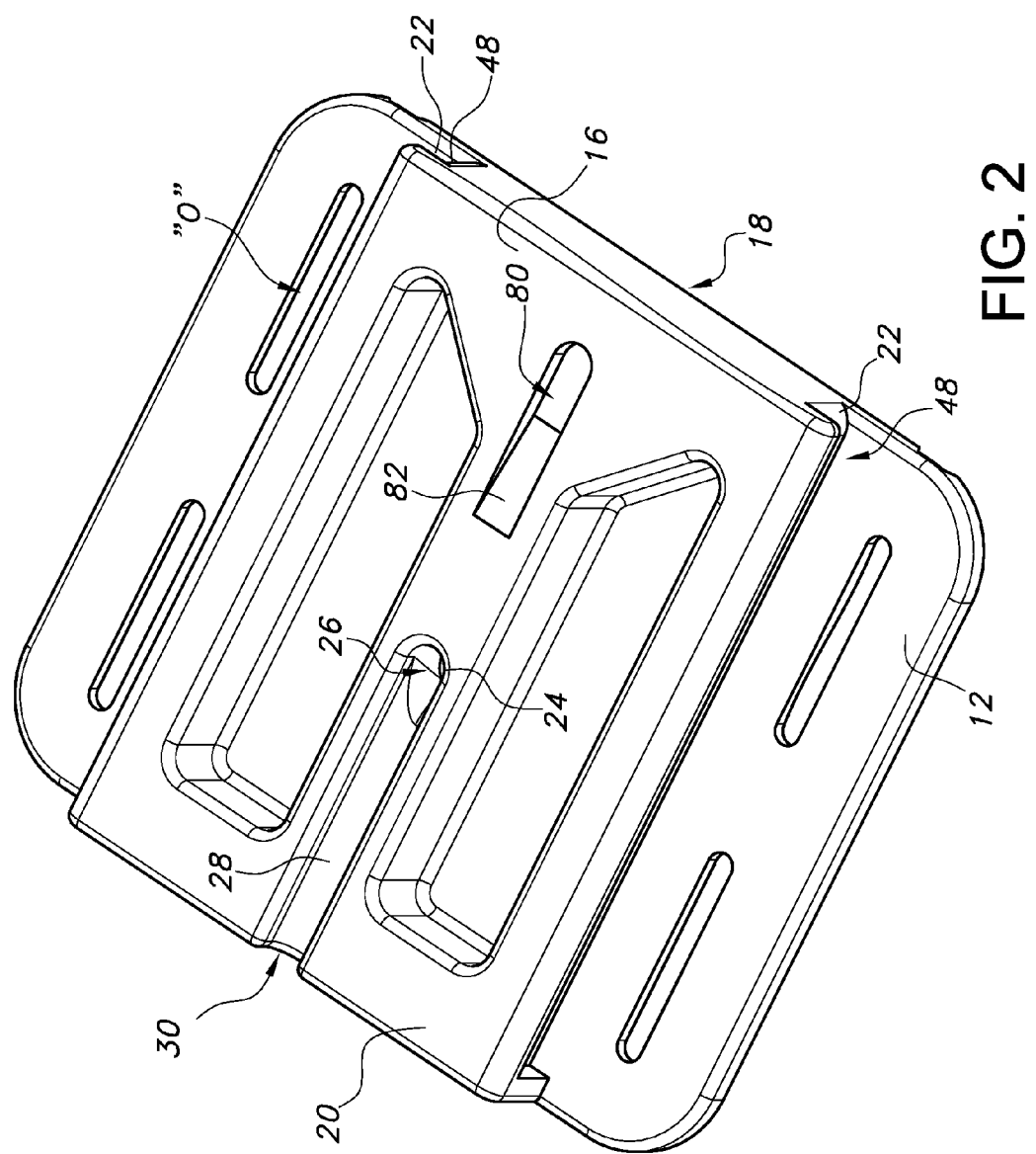
FIG. 2 shows a top perspective view of a detail of a base of an exemplary catheter-positioning slide cover clamp assembly.

Turning now to the drawings, the invention is generally illustrated in exploded side perspective view at FIG. 1 which shows an exemplary catheter clamp assembly 10 that includes a base 12 and a slide cover 14. The base 12 includes a top 16, a bottom 18, and a body 20 having a slide cover track 22. The body 18 has internal walls 24 defining a catheter opening 26 extending from the top 16 to the bottom 18. The body 20 further defines a catheter channel 28 extending from the catheter opening 26 to a sidewall exit 30. The internal walls 24 defining the catheter opening 26 may further define a generally curved transition 32 between the catheter opening 26 and the catheter channel 28. FIG. 2 is a top perspective view of a base 12 without the associated slide cover. As illustrated in FIG. 2, the catheter channel 28 extends from the catheter opening 26 to a sidewall exit 30. Also visible in FIG. 2 is a notch 80 which will be described later. FIG. 2 and many of the other drawings include a series of openings "O" along the base which may be used to suture the catheter clamp assembly 10 to a patient or to enhance the connection between the catheter clamp assemblies 10 to an anchor pad 200 illustrated in FIG. 13.

Figure 3:
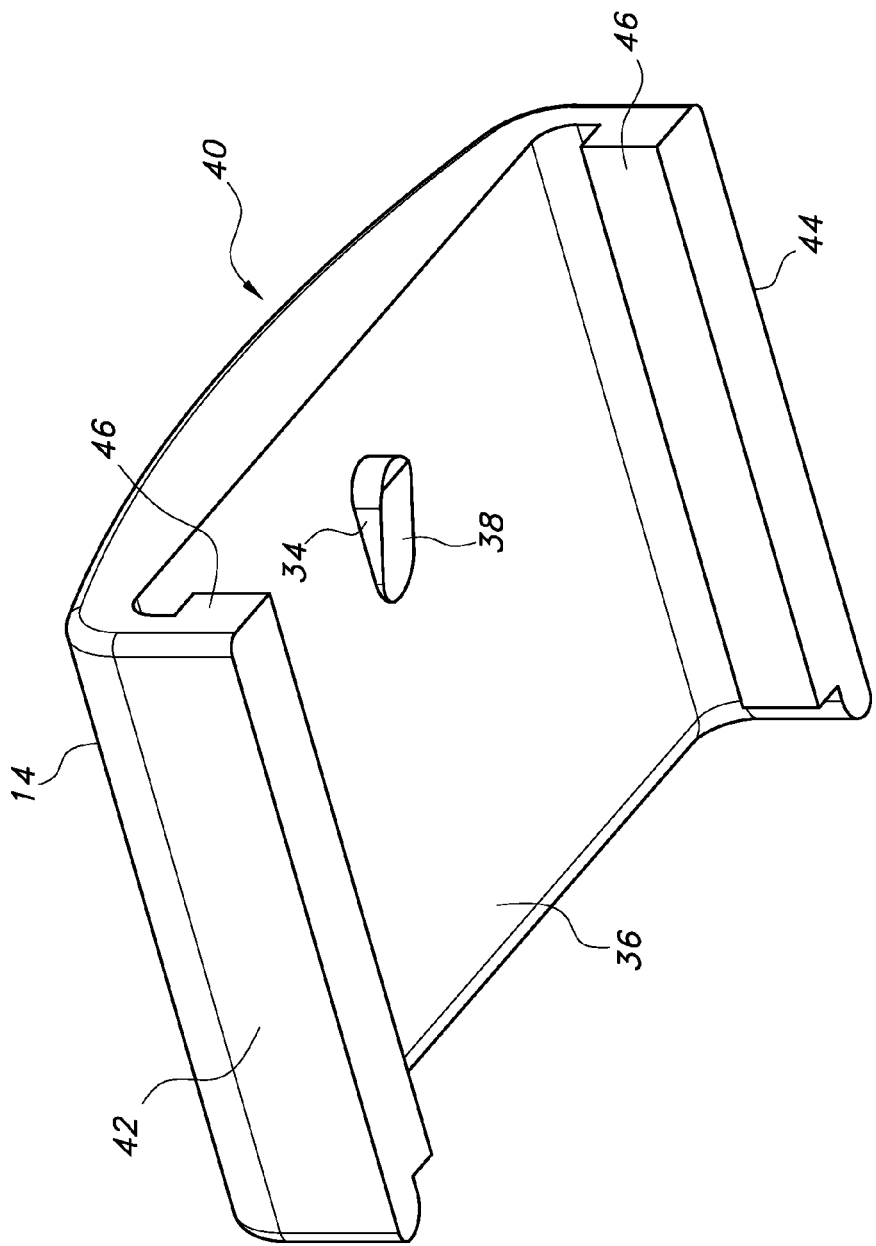
FIG. 3 shows a bottom perspective view of a detail of a slide cover of an exemplary catheter-positioning slide cover clamp assembly.
Figure 4:
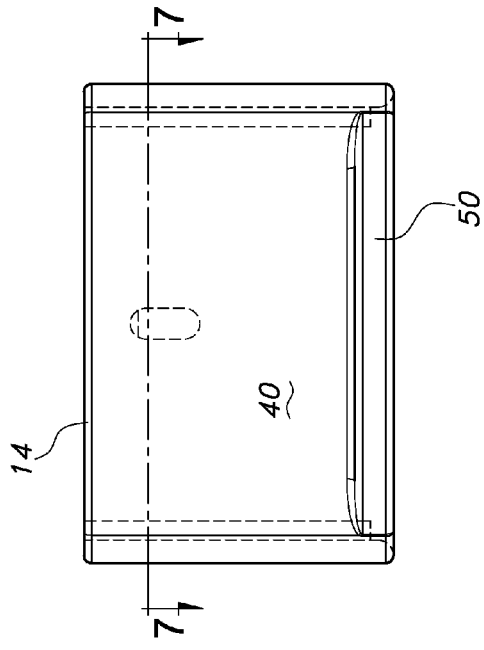
FIG. 4 shows a bottom view of a detail of a slide cover of an exemplary catheter-positioning slide cover clamp assembly.
Figure 5:
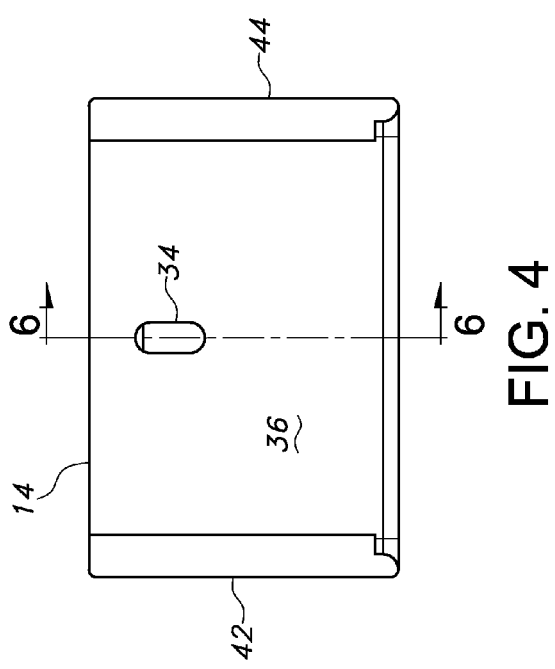
FIG. 5 shows a top view of a detail of a slide cover of an exemplary catheter-positioning slide cover clamp assembly.
Figure 6:
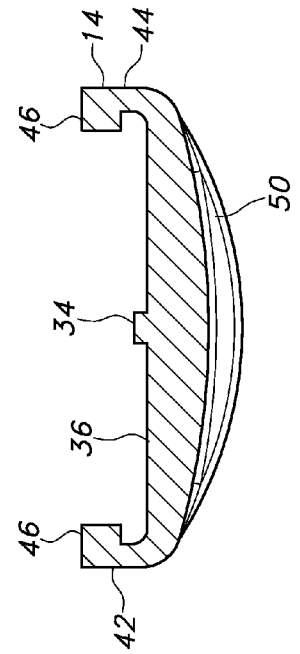
FIG. 6 shows a side cross-section view of the slide cover of FIG. 4 taken along line 6-6.
Figure 7:
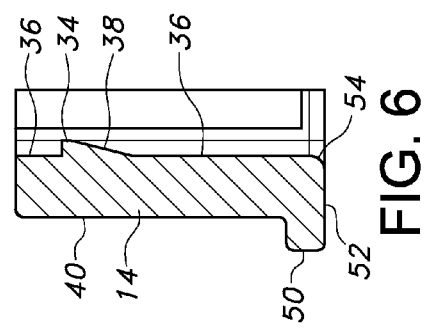
FIG. 7 shows a side cross-section view of the slide cover of FIG. 5 taken along line 7-7.

Referring to FIGS. 3 to 7, there are shown details of an exemplary slide cover. FIG. 3 is a bottom perspective view of an exemplary slide cover 14 that includes a prong 34 extending from a lower surface 36 of the slide cover. The prong 34 may have an inclined portion 38 to engage with a portion of the internal walls defining the catheter opening and for clamping a catheter in the catheter channel. The slide cover 14 may further include an upper surface 40, a first edge 42 and an opposed second edge 44. The slide cover 14 may incorporate catches 46 on the first and second edges 42, 44 for slidably engaging the slide cover 14 with the slide track 22 which may be recesses 48 defined in the body 20 of the base 12. FIG. 4 is a bottom view of an exemplary slide cover 14. The relative position of the prong 34 extending from the bottom surface 36 is visible in this bottom view. FIG. 5 is a top view of an exemplary slide cover 14. The slide cover may include a lip or projection 50 for better engaging the finger of a user when applying force to slide the slide cover 14. This lip or projection 50 may extend from an upper surface 40 of the slide cover 14. FIG. 6 is a side cross-section view of the exemplary slide cover 14 taken along line 6-6. It illustrates the lip or projection 50 and an edge 52 having curved or chamfered portion 54 for contacting a catheter. For example the edge 52 may be identified as a third edge 52 that is generally perpendicular to the first edge 42 and the second edge 44. FIG. 7 is a rear cross-section view of the exemplary slide cover 14 taken along line 7-7. It illustrates that the slide cover 14 may incorporate catches 46 on the first and second edges 42, 44 for slidably engaging the slide cover 14 with the slide track 22. FIG. 7 also illustrates the prong 34 extending from the bottom surface 36 of the slide cover 14. Suitable materials for the catheter clamp assembly can be polymeric materials such as polyethylene, polypropylene, polyester, nylon, polyether ether ketone (PEEK) and the like, as well as any combination thereof.

Figure 8:
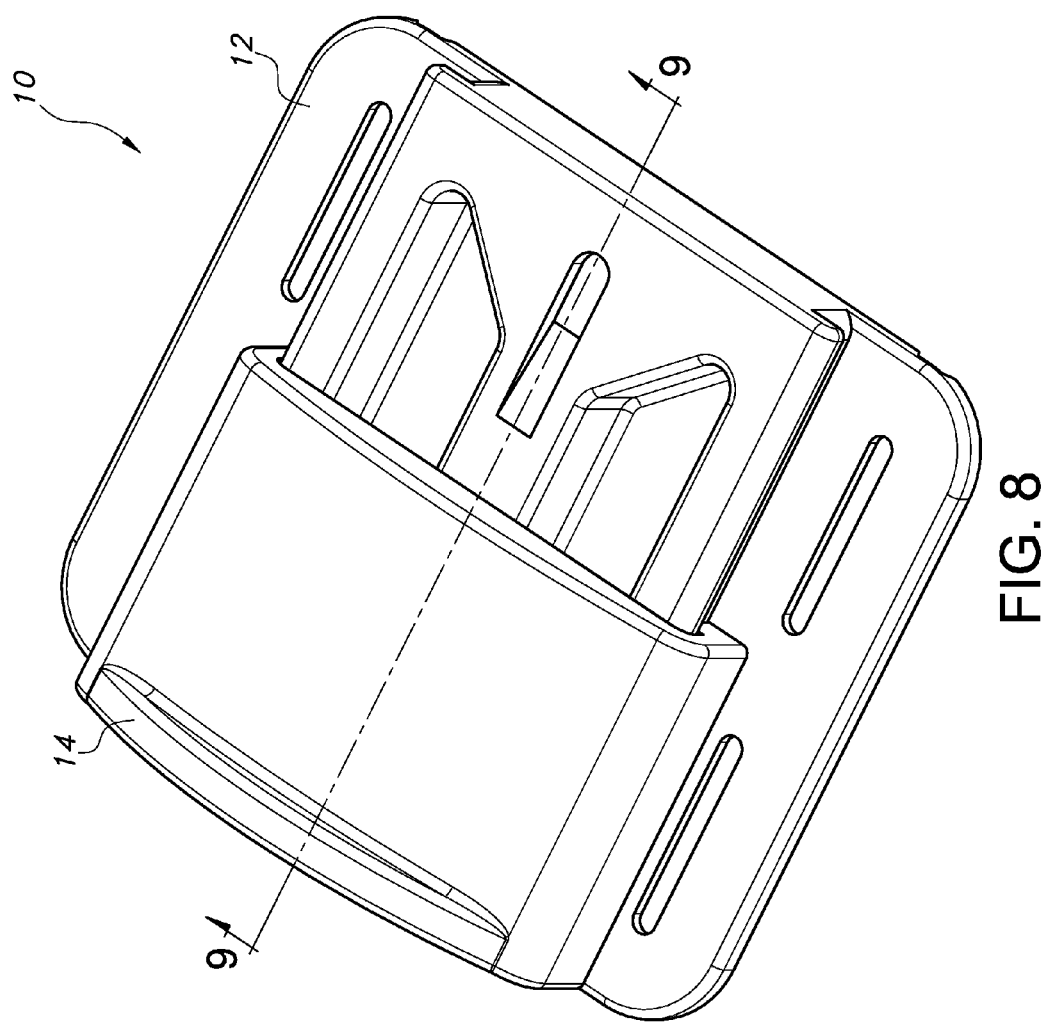
FIG. 8 shows a perspective view of an exemplary catheter-positioning slide cover clamp assembly.
Figure 9:
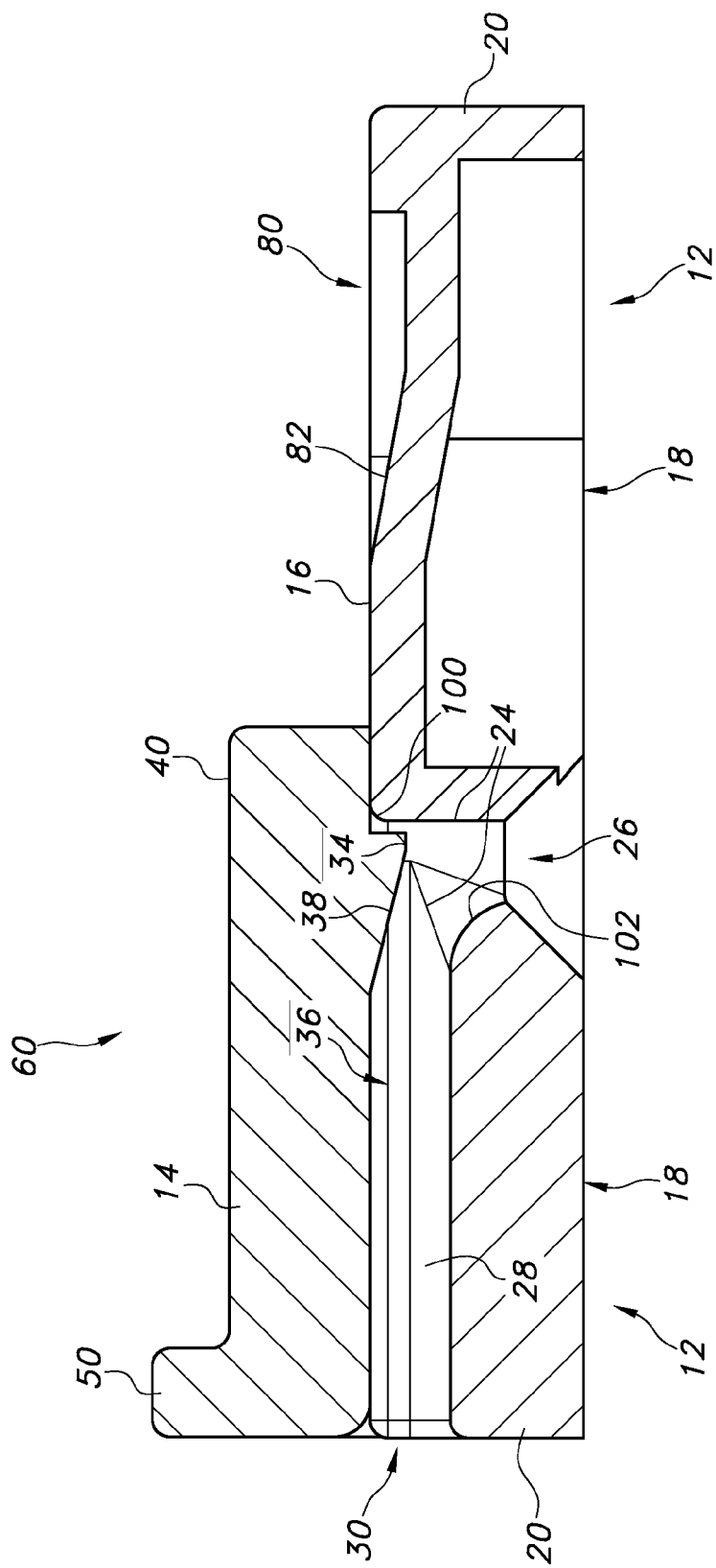
FIG. 9 shows a side cross-section view of the exemplary catheter-positioning slide cover clamp assembly of FIG. 8 taken along line 9-9 showing the slide cover in a second position.

FIG. 8 is a top perspective view of an exemplary catheter clamp assembly 10 with the slide cover 14 slidably engaged with the base 12. In FIG. 8, the slide cover is in a second location 60 in which the slide cover 14 is configured to securely clamp a catheter in the catheter channel 28. FIG. 9 is a side cross-section view of the exemplary catheter clamp assembly 10 of FIG. 8 taken along line 9-9. As can be seen in FIG. 9, the slide cover 14 overlays the catheter channel 28 and the prong 34 extending from the bottom surface 36 is configured to engage the wall 24 of the catheter opening 26 at least at an engagement point 100 to hold the slide cover 14 securely in the second location 62 as the inclined portion 38 of the prong 34 is configured to secure a catheter in the catheter channel 28. Desirably, the internal walls 24 defining the catheter opening 26 further define a transition 102 between the catheter opening 26 and catheter channel 28. This transition 102 is desirably a curved or rounded transition 102 which prevents kinking or pinching of a catheter.

Figure 10:
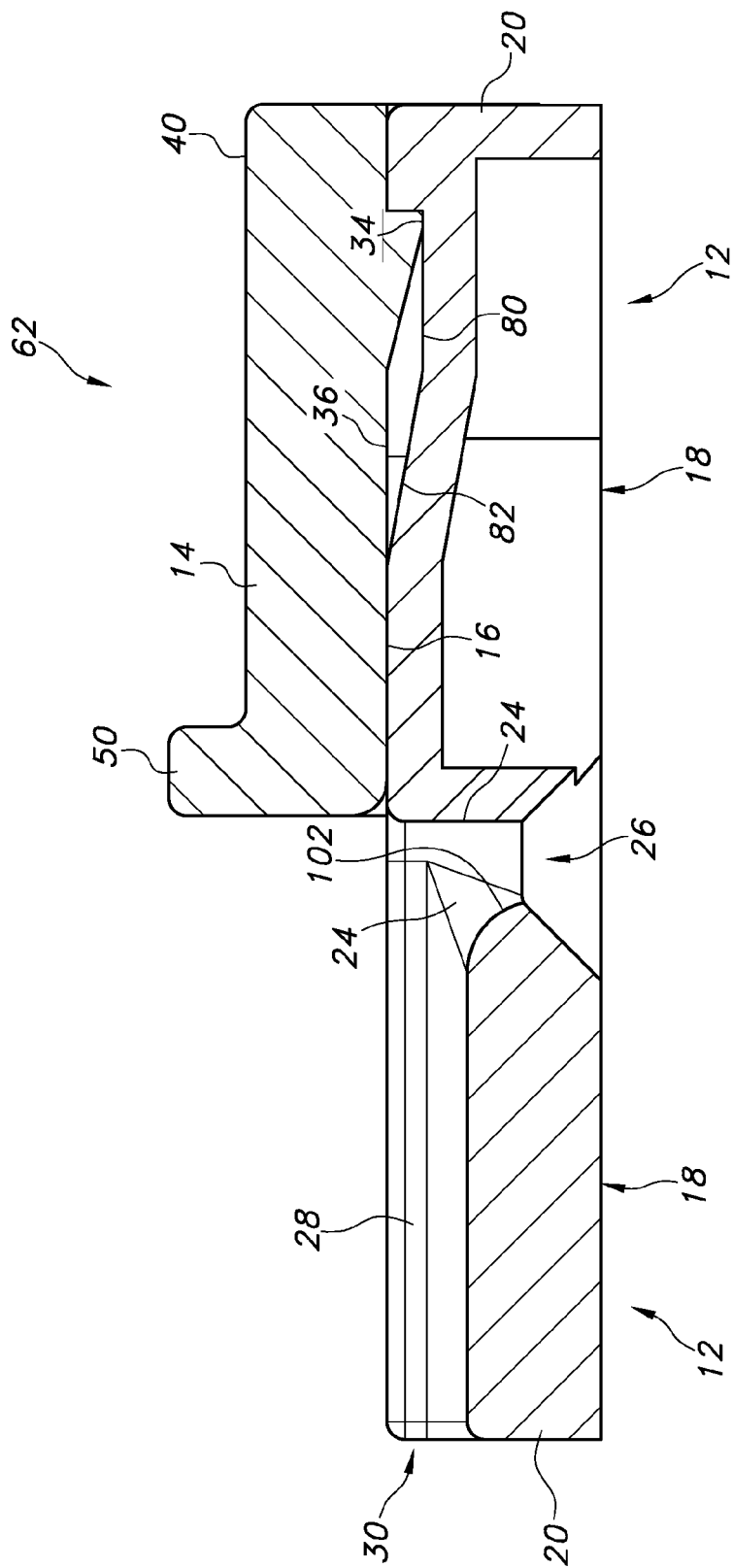
FIG. 10 shows a side cross-section view of the exemplary catheter-positioning slide cover clamp assembly of FIG. 8 taken along line 9-9 except that the slide cover is shown in a first position.

FIG. 10 is a representation of the side cross-section view illustrated by FIG. 9 in which the slide cover 14 is in its first location for providing access to thread a catheter into and through the catheter opening 26. As can be seen from FIGS. 9 and 10, the base of the catheter opening 26 may be conical or cone-shaped to ease threading of a catheter into the catheter opening 26 from the bottom 18 of the base 12. The top surface 16 of the base 12 may desirably include a notch 80 for receiving the prong 34 extending from the lower surface 36 of the slide cover 12. The notch 80 desirably has an inclined portion 82 and is located on the top surface 16 of the base in a location to releasably hold the slide cover 14 in its first location 62.

Figure 11A:
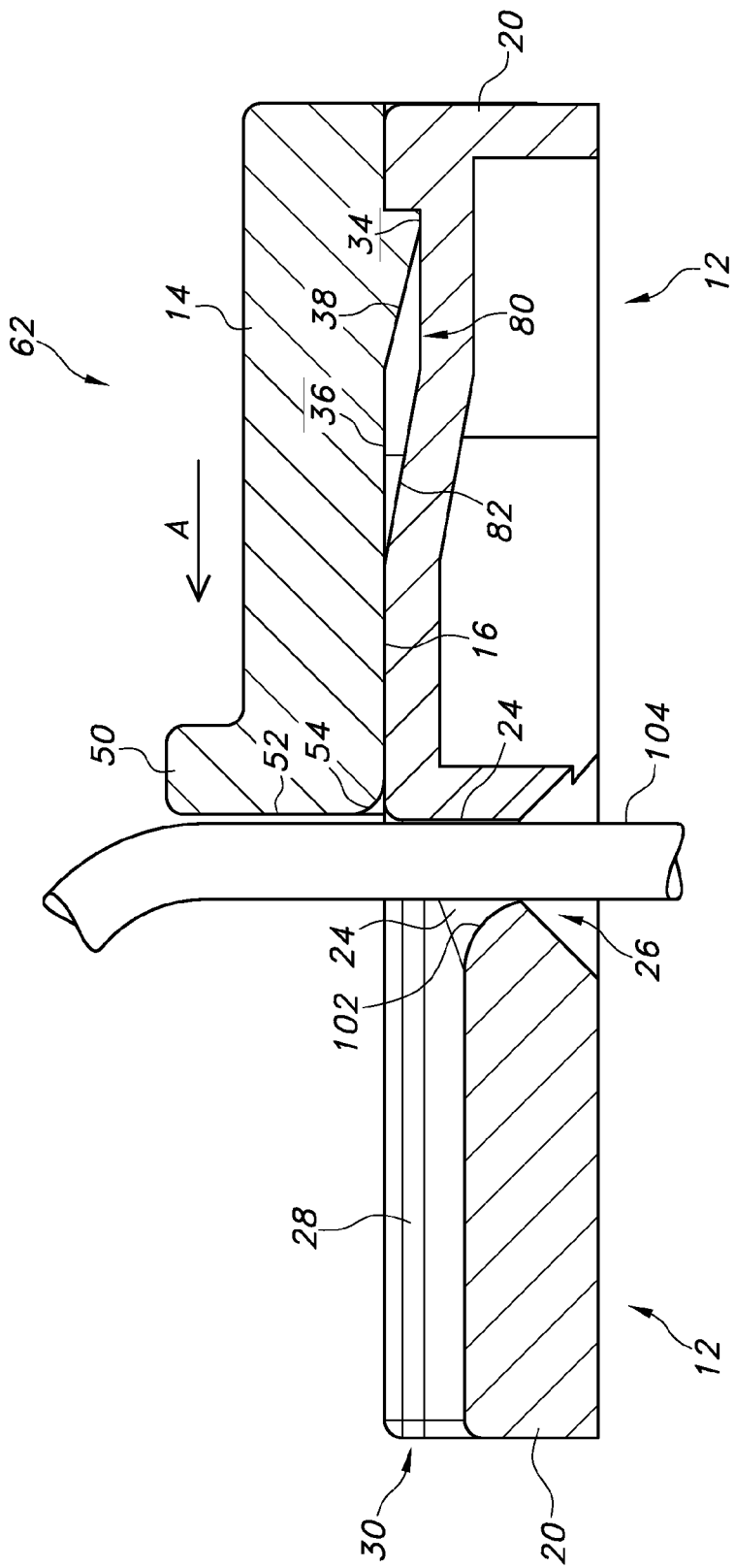
FIG. 11A shows a side cross-section view of an exemplary catheter-positioning slide cover clamp assembly and a catheter threaded through the catheter opening with the slide cover shown in a first position.
Figure 11B:
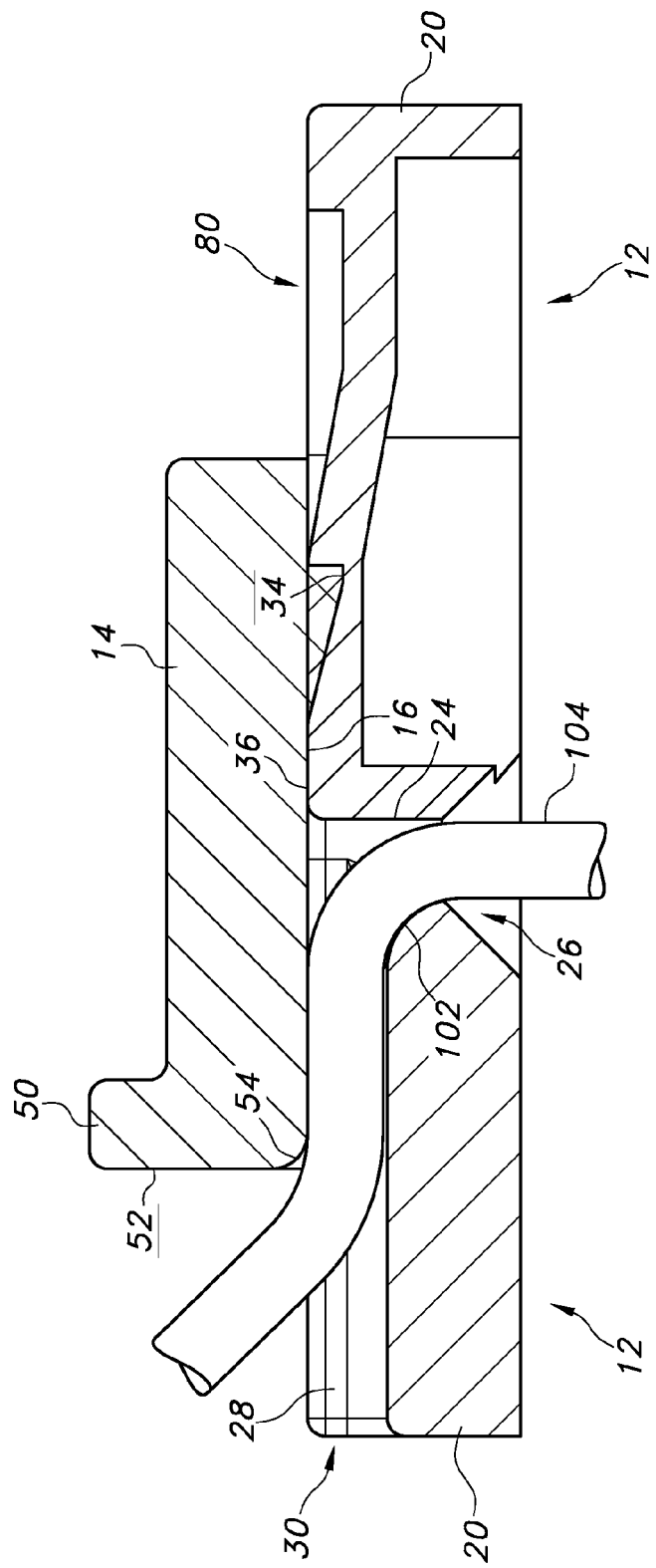
FIG. 11B shows a side cross-section view of an exemplary catheter-positioning slide cover clamp assembly and a catheter threaded through the catheter opening with slide cover is shown moving in the direction of the arrow "A" between a first position and a second position.
Figure 11C:
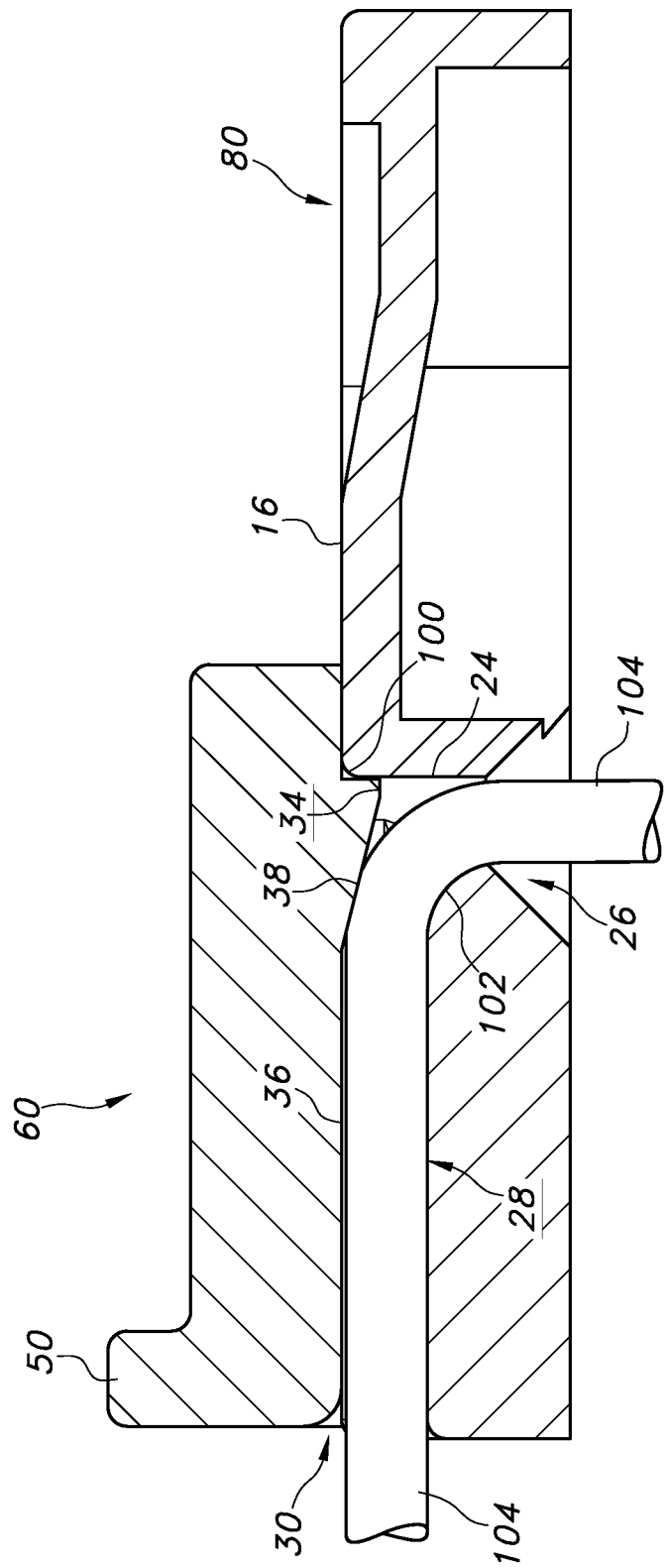
FIG. 11C shows a side cross-section view of an exemplary catheter-positioning slide cover clamp assembly and a catheter threaded through the catheter opening with the slide cover shown in a second position.

FIGS. 11A to 11C illustrate, in side cross-section views, the sequence of moving the slide cover 14 from its first location 62 to its second location 60 in the direction of the arrow "A" which simultaneously contacts a length of a catheter 104 extending through the catheter opening 26 and positions it in the catheter channel 28 for securement by the slide cover 14 when it reaches its second location 60. More particularly, a force is applied against the lip or projection 50 of the slide cover 14 to urge the slide cover in the direction of the arrow "A". The force must be sufficient to overcome friction and mechanical engagement between the prong 34 and the notch 80 that releasably holds the slide cover 14 in its first position 62. Desirably the inclined portion 38 of the prong 34 and the inclined portion 82 of the notch 80 work together to help overcome the friction and mechanical engagement so that a user may apply sufficient force with a finger. As can be seen in FIG. 11A, the catheter 104 extends substantially vertically out of the catheter opening 26. That is, the portion of the catheter 104 immediately adjacent the catheter opening 26 has an orientation that is parallel with the catheter opening 26 and which can be described as "vertical" or perpendicular to the plane of the base 12.

FIG. 11B illustrates partial travel of the slide cover 14 from its first location 62 to its second location 60. In this view, a curved or chamfered portion 54 of an edge 52 of the slide cover 14 contacts the catheter 104 extending through the catheter opening 26 and, as the slide cover is moved from its first location 62 to its second location 60, translates the generally "vertical" orientation of the catheter 104 (i.e., perpendicular to the plane of the base 12) to a generally "horizontal" orientation (i.e., parallel to the plane of the base 12) such that the slide cover 14 positions the catheter 104 in the catheter channel 28. Because of the very small clearance between the lower surface 36 of the slide cover 14 and the top 16 of the base 12 (especially in the area adjacent the catheter channel 28), the curved portion 54 of the slide cover edge 52 drives the catheter 104 into the catheter channel 28 without pinching or kinking the catheter. Importantly, this movement simultaneously positions the catheter in the catheter channel and moves the slide cover to its second position which ultimately secures or clamps the catheter in the catheter channel to prevent movement of the catheter relative to the catheter clamp assembly.

FIG. 11C illustrates the slide cover 12 in its second location 60 in which the catheter 104 is secured in the catheter channel 28. The inclined portion 38 of the prong 34 pushes the catheter 104 against the walls defining the catheter channel 28. It is contemplated that ribs (not shown) may be included in the channel to help increase the engagement between the catheter 104 and the walls defining the catheter channel 28. Alternatively and/or additionally, the catheter channel 28 may be formed of or may include a high friction material such as a relatively high friction silicone material. It is also contemplated that the prong 36 or at least a catheter contacting portion of the prong 36 may be made of a high friction material. The prong 36 engages with a wall 24 defining the catheter opening 26 at an engagement point 100 to hold the slide cover 14 securely in the second location 62 as the inclined portion 38 of the prong 34 is configured to secure a catheter in the catheter channel 28. The slide cover 14 may be moved from its second position 60 to its first position 62 by applying a force to the slide cover in the direction opposite the arrow "A" illustrated in FIGS. 11A and 11B.

Figure 12A:
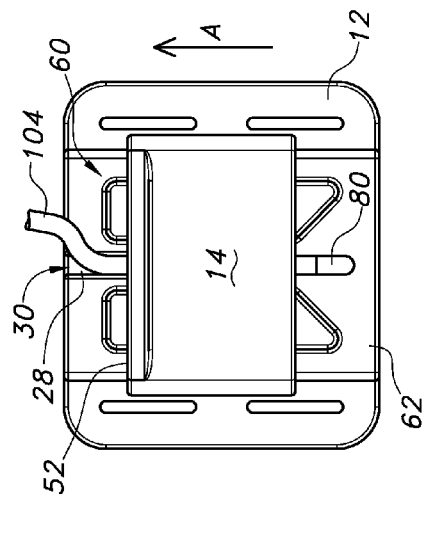
FIGS. 12A, 12B and 12C are top views of an exemplary catheter-positioning slide cover clamp assembly and a catheter threaded through the catheter opening with the slide cover shown moving in sequence from a first position in FIG. 12A to a second position in FIG. 12C.
Figure 12B:
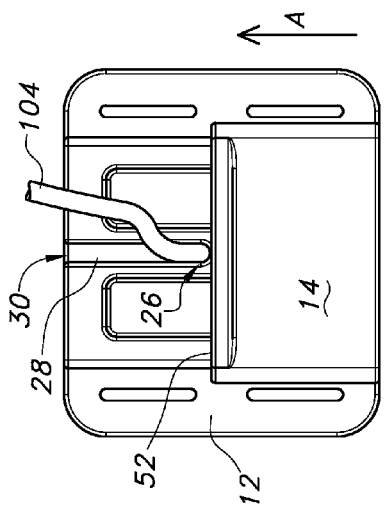
Figure 12C:
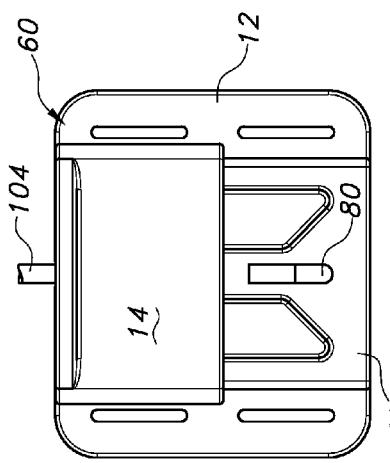

Referring to FIGS. 12A to 12C, there is shown in top view the sequence of moving the slide cover 14 from its first location 62 to its second location 60 in the direction of the arrow "A" which simultaneously contacts a length of a catheter 104 extending through the catheter opening 26 and positions it in the catheter channel 28 for securement by the slide cover 14 when it reaches its second location 60. More particularly, a force is applied against the lip or projection 50 of the slide cover 14 to urge the slide cover in the direction of the arrow "A".

As can be seen in FIG. 12A, the catheter 104 extends out of the catheter opening 26. That is, the portion of the catheter 104 immediately adjacent the catheter opening 26 in a manner that is not aligned with the catheter channel 28 defined by the walls of the base 12. FIG. 12B illustrates partial travel of the slide cover 14 from its first location 62 to its second location 60. A curved or chamfered portion (not shown) of an edge 52 of the slide cover 14 contacts the catheter 104 extending through the catheter opening 26 and, as the slide cover is moved from its first location 62 to its second location 60, the edge 52 of the slide cover aligns the catheter 104 with the catheter channel 28. Because of the very small clearance between the lower surface 36 of the slide cover 14 and the top 16 of the base 12 (especially in the area adjacent the catheter channel 28), the curved portion of the slide cover edge 52 both aligns the catheter 104 with the catheter channel and drives the catheter 104 into the catheter channel 28 without pinching or kinking the catheter. This clearance is much less than the diameter of the catheter and is desirably 0.25 millimeters or less. For example, the clearance may be from about 0.01 millimeters to 0.25 millimeters. As another example, the clearance may be from about 0.05 millimeters to 0.20 millimeters. Importantly, this movement simultaneously positions the catheter in the catheter channel and moves the slide cover to its second position which ultimately secures or clamps the catheter in the catheter channel to prevent movement of the catheter relative to the catheter clamp assembly. FIG. 12C illustrates the slide cover 12 in its second location 60 in which the catheter 104 is secured in the catheter channel 28. The slide cover 14 may be moved from its second position 60 to its first position 62 by applying a force to the slide cover in the direction opposite the arrow "A" illustrated in FIGS. 12A and 12B.

Figure 13:
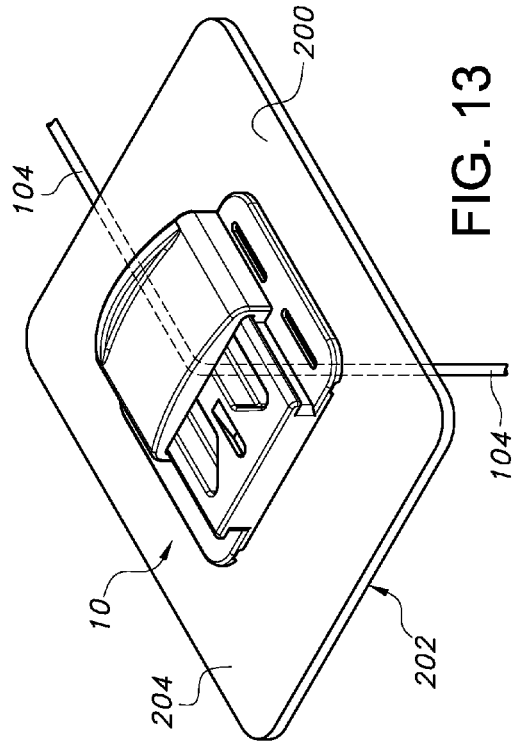
FIG. 13 is a perspective view of an exemplary catheter-positioning slide cover clamp assembly and a catheter threaded through the catheter opening with the slide cover shown a second position and in which the slide cover clamp assembly is joined with an anchor pad.

Referring to FIG. 13 of the drawings, there is shown in perspective view an exemplary catheter clamp assembly 10 including an anchor pad 200. A catheter 104 is illustrated to provide an example of how the catheter 104 may be threaded or utilized in the catheter clamp assembly 10. The anchor pad 200 may be any suitable substantially flat piece of material. The proximal, or lower, side 202 of the pad faces toward the skin of the patient, and is desirably covered with an adhesive surface suitable for attaching the anchor pad 200 to the skin of the patient. The upper side 204 of the anchor pad faces away from the skin of the patient and supports the catheter clamp assembly. The anchor pad 200 desirably is composed of a laminate structure with an upper foam layer (e.g., closed-cell polyethylene foam) and a lower adhesive layer. The lower adhesive layer constitutes the lower surface of the anchor pad. The lower surface desirably is a medical-grade adhesive. Such foams with an adhesive layer are available commercially from a variety of manufacturers.

A surface of the upper foam layer may constitute the upper surface of the anchor pad. The upper surface can be roughened by chemical priming or corona-treating the foam with a low electric charge. The roughened or porous upper surface can improve the quality of the adhesive joint (which is described below) between the base of the catheter clamp assembly and the anchor pad. In alternative examples, the flexible anchor pad can include a medical-grade adhesive lower layer, an inner foam layer and an upper paper or other woven or nonwoven cloth layer.

The lower surface of the anchor pad may include a region of hydro-colloid adhesive disposed centrally on the anchor pad in the region corresponding to the catheter opening 26. This hydro-colloid region provides an adhesive which is less irritating to sensitive skin on the portion of the anchor pad which is closest to the catheter insertion site.

A removable paper or plastic release liner desirably covers the adhesive lower surface before use. The release liner desirably resists tearing and desirably is divided into a plurality of pieces to ease attachment of the anchor pad to a patient's skin. For example, the release liner may be split along a centerline of the anchor pad in order to expose only half of the adhesive lower surface at one time.

The length of each release liner piece may extend beyond a centerline of the anchor pad and may be folded over, or back onto the release liner. This folded over portion defines a pull-tab to facilitate removal of the release liner from the adhesive lower surface. A healthcare worker uses the pull-tab by grasping and pulling on it so that the release liner is separated from the lower surface. The pull-tab eliminates the need to pick at a corner edge or other segment of the release liner in order to separate the release liner from the adhesive layer. The pull-tab can be designed in a variety of configurations. For example, the pull-tab need not be located along a centerline of the anchor pad; rather, the pull-tab can be located along any line of the anchor pad in order to ease the application of the anchor pad onto the patient's skin at a specific site.

The present invention encompasses a catheter system composed of a flexible catheter 104 and a catheter clamp assembly 10 as generally described above. This catheter system is advantageous at least because it allows for ease of threading the catheter through a catheter opening at the bottom of the catheter clamp assembly when the catheter opening has a frusto-conical shape. Moreover, the catheter system provides proper catheter positioning in the catheter clamp assembly essentially simultaneously with the movement of the catheter clamp assembly to the location that secures the catheter in the catheter clamp assembly. Exemplary catheters include infusion catheters such as those described at, for example, by U.S. Pat. No. 6,350,253; U.S. Pat. No. 7,004,923; U.S. Pat. No. 7,438,711; U.S. Pat. No. 7,452,353; U.S. Pat. No. 7,527,609; U.S. Pat. No. 7,547,302; U.S. Pat. No. 7,780,638; U.S. Pat. No. 8,328,771; and U.S. Pat. No. 8,343,135; the contents of each are incorporated herein by reference.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A catheter clamp assembly comprising:
   a base that includes:
   a top and a bottom,
   a body that includes a slide cover track extending from a first end of the body to a second end of the body, the body having internal walls defining a catheter opening extending from the bottom to the top, the body further defining a catheter channel extending from the catheter opening to a sidewall opening; and
   a slide cover slidably engaged with the slide cover track, the slide cover including a prong extending from a lower surface of the slide cover to engage a wall defining the catheter opening and to secure a catheter in the catheter channel;
   wherein the slide cover has a first location atop the body that includes a first end of the slide cover aligning with the first end of the body providing access to thread a catheter through the catheter opening and a second location atop the body that includes a second end of the slide cover aligning with the second end of the body that securely clamps a catheter in the catheter channel, such that sliding the slide cover from its first location to its second location contacts a length of a catheter extending through the catheter opening and positions the catheter in the catheter channel for securement when the slide cover reaches its second location.

2. The clamp assembly of claim 1, wherein the slide cover track in the body of the base is a pair of opposed sides having recesses defined therein and the slide cover has a first edge and an opposed second edge, each edge including catches for slidably engaging the slide cover with the recesses.

3. The clamp assembly of claim 1, wherein the slide cover includes an edge having a curved catheter contacting portion.

4. The clamp assembly of claim 1, wherein the internal walls defining the catheter opening further define a curved transition between the catheter opening and the catheter channel.

5. The clamp assembly of claim 2, wherein the recesses defined in the pair of opposed sides of the body of the base further include stops at one end thereof.

6. The clamp assembly of claim 1, wherein the top surface of the base further includes notch for receiving the prong extending from the lower surface of the slide cover, the notch being located on the top surface of the base to releasably hold the slide cover in its first location.

7. The clamp assembly of claim 1, wherein the slide cover includes a lip.

8. The clamp assembly of claim 1, wherein the prong on the slide cover has an inclined portion.

9. The clamp assembly of claim 1, wherein the top of the base and the bottom surface of the slide cover define generally planar surfaces having a clearance of less than 0.25 millimeter.

10. A catheter system comprising:
    a flexible catheter; and
    a catheter clamp assembly comprising:
    a base that includes:
    a bottom and a top,
    a body having a slide cover track extending from a first end of the body to a second end of the body, the body having internal walls defining a catheter opening extending from the bottom to the top, the body further defining a catheter channel extending from the catheter opening to a sidewall exit; and
    a slide cover slidably engaged with the slide cover track, the slide cover including a prong extending from the lower surface of the cover to engage with a wall defining the catheter opening and for clamping a catheter in the catheter channel;
    wherein the slide cover has a first location atop the body that includes a first end of the slide cover aligning with the first end of the body for providing access to thread a catheter through the catheter opening and a second location atop the body that includes a second end of the slide cover aligning with the second end of the body that securely clamps a catheter in the catheter channel, such that sliding the slide cover from its first location to its second location simultaneously contacts a length of a catheter extending through the catheter opening and positions the catheter in the catheter channel for securement by the slide cover when it reaches its second location.

11. The clamp assembly of claim 10, wherein the slide cover track in body of the base is a pair of opposed sides having recesses defined therein and the slide cover has a first edge and an opposed second edge, each edge including catches for slidably engaging the cover with the recesses.

12. The clamp assembly of claim 10, wherein the slide cover includes an edge having a curved portion for contacting a catheter.

13. The clamp assembly of claim 10, wherein the internal walls defining the catheter opening further define a curved transition between the catheter opening and catheter channel.

14. The clamp assembly of claim 11, wherein the recesses defined in the pair of opposed sides of the body of the base further include stops at one end thereof.

15. The clamp assembly of claim 10, wherein the top surface of the base further includes a notch for receiving the prong extending from the lower surface of the slide cover, the notch being located on the top surface of the base to releasably hold the slide cover in its first location.

16. The clamp assembly of claim 10, wherein the slide cover includes a lip.

17. The clamp assembly of claim 10, wherein the prong on the slide cover has an inclined portion for engaging a catheter.

18. The clamp assembly of claim 10, wherein the top of the base and the bottom of the slide cover define generally planar surfaces having a clearance of less than 0.25 millimeter.

19. A catheter clamp assembly comprising:
a base that includes:
a bottom and a top,
a body having a pair of opposed sides having recesses defined therein, the recesses defining a slide cover track extending from a first end of the body to a second end of the body, the body having internal walls defining a catheter opening extending from the bottom to the top, the body further defining a catheter channel extending from the catheter opening to a sidewall exit; and
a slide cover including:
an upper surface and a lower surface, a first edge and an opposed second edge, and catches located on the first and second edges to slidably engage the cover with the recesses defined in the body of the base,
a prong extending from the lower surface of the cover to engage with a wall defining the catheter opening and for clamping a catheter against the catheter channel;
wherein the slide cover has a first location atop the body that includes a first end of the slide cover aligning with the first end of the body providing access to thread a catheter through the catheter opening and a second location atop the body that includes a second end of the slide cover aligning with the second end of the body that securely clamps a catheter in the catheter channel, such that sliding the slide cover from its first location to its second location simultaneously contacts a length of a catheter extending generally in a first direction through the catheter opening and positions the catheter in a second, generally perpendicular direction with respect to the first direction in the catheter channel for securement when the slide cover reaches its second location.

20. The clamp assembly of claim 19, wherein the internal walls defining the catheter opening further define a curved transition between the catheter opening and the catheter channel.

* * * * *